United States Patent
Cattaneo et al.

(10) Patent No.: US 12,161,782 B2
(45) Date of Patent: Dec. 10, 2024

(54) MEDICAL DEVICE AND COATING WITH BONDING AGENT

(71) Applicant: Acandis GmbH, Pforzheim (DE)

(72) Inventors: Giorgio Cattaneo, Karlsruhe (DE); Hans Peter Wendel, Balingen (DE)

(73) Assignee: Acandis GmbH, Pforzheim (DE)

( * ) Notice: Subject to any disclaimer, the term of this patent is extended or adjusted under 35 U.S.C. 154(b) by 1073 days.

(21) Appl. No.: 17/052,286

(22) PCT Filed: May 2, 2019

(86) PCT No.: PCT/EP2019/061173
§ 371 (c)(1),
(2) Date: Nov. 2, 2020

(87) PCT Pub. No.: WO2019/211345
PCT Pub. Date: Nov. 7, 2019

(65) Prior Publication Data
US 2021/0085835 A1 Mar. 25, 2021

(30) Foreign Application Priority Data
May 3, 2018 (DE) ..................... 10 2018 110 591.6

(51) Int. Cl.
*A61L 31/10* (2006.01)
*A61L 31/02* (2006.01)
*A61L 31/16* (2006.01)

(52) U.S. Cl.
CPC ............. *A61L 31/10* (2013.01); *A61L 31/022* (2013.01); *A61L 31/16* (2013.01);
(Continued)

(58) Field of Classification Search
CPC ...... A61F 2/86; A61F 2/90; A61F 2310/0037; A61F 2/82; A61L 33/0011; A61L 31/02; A61L 31/10; A61L 31/16; A61L 31/046
See application file for complete search history.

(56) References Cited

U.S. PATENT DOCUMENTS

| 5,554,182 A | 9/1996 | Dinh et al. |
| 6,251,135 B1 * | 6/2001 | Stinson ..................... A61F 2/82 623/1.34 |

(Continued)

FOREIGN PATENT DOCUMENTS

| CN | 101234046 | 8/2008 |
| CN | 103228317 | 7/2013 |

(Continued)

OTHER PUBLICATIONS

International Search Report and Written Opinion issued in PCT/EP2019/061173, mailed Jul. 24, 2019.
(Continued)

*Primary Examiner* — Christopher D. Prone
(74) *Attorney, Agent, or Firm* — HSML P.C.

(57) ABSTRACT

The invention relates to a medical device for use in human vessels, in particular in the carotid artery, comprising: a self-expandable mesh structure which at least partially forms a curved wall, and has, in a radially compressed state, a cross-sectional diameter of not more than 2.5 mm, wherein the mesh structure is formed of at least one mesh structural element which has a height that is no more than 200 µm, in particular no more than 150 µm, preferably no more than 70 µm, where the height is measurable along a diameter of the mesh structure, and wherein the mesh structure is at least partially formed of a nickel titanium alloy and is at least partially coated in fibrin.

22 Claims, 3 Drawing Sheets

(52) U.S. Cl.
CPC ..... *A61L 2300/236* (2013.01); *A61L 2300/42* (2013.01); *A61L 2400/16* (2013.01)

(56) References Cited

U.S. PATENT DOCUMENTS

| | | | |
|---|---|---|---|
| 6,254,632 | B1 | 7/2001 | Wu et al. |
| 6,599,558 | B1 * | 7/2003 | Al-Lamee ............... A61L 31/10 427/407.1 |
| 2001/0049549 | A1 | 12/2001 | Boylan et al. |
| 2002/0035394 | A1 | 3/2002 | Fierens et al. |
| 2003/0139797 | A1 | 7/2003 | Johnson et al. |
| 2005/0058688 | A1 | 3/2005 | Boerger et al. |
| 2007/0100426 | A1 | 5/2007 | Rudakov et al. |
| 2007/0168019 | A1 | 7/2007 | Amplatz et al. |
| 2013/0267762 | A1 | 10/2013 | Levy et al. |
| 2016/0354099 | A1 | 12/2016 | Turjman et al. |
| 2017/0239033 | A1 | 8/2017 | Frid |
| 2018/0042738 | A1 | 2/2018 | Sun et al. |
| 2018/0228590 | A1 | 8/2018 | Frid |

FOREIGN PATENT DOCUMENTS

| | | | |
|---|---|---|---|
| CN | 106572900 | | 4/2017 |
| CN | 107920883 | | 4/2018 |
| DE | 69623855 | T2 | 5/2003 |
| DE | 102009023661 | A1 | 12/2010 |
| DE | 102014115533 | A1 | 4/2016 |
| EP | 0357003 | A2 | 3/1990 |
| EP | 0 566 245 | | 10/1993 |
| EP | 1330993 | A1 | 7/2003 |
| EP | 2029066 | B1 | 3/2011 |
| EP | 2987463 | A1 | 2/2016 |
| EP | 2796112 | B1 | 11/2016 |
| EP | 2157937 | B1 | 3/2017 |
| GB | 2344053 | A | 5/2000 |
| TW | 201742605 | A | 12/2017 |
| WO | 0168158 | A1 | 9/2001 |
| WO | 2005094725 | A1 | 10/2005 |
| WO | 2012061193 | A2 | 5/2012 |
| WO | WO-2017042335 | A1 * | 3/2017 ............... A61F 2/01 |
| WO | 2017121803 | A1 | 7/2017 |
| WO | 2018039444 | A1 | 3/2018 |
| WO | 2018050262 | A1 | 3/2018 |

OTHER PUBLICATIONS

Riedelova-Reicheltova, et al., "Fibrin Nanostructures for Biomedical Applications", Physiol.Res. 65 (Suppl. 2): S263-S273, Sep. 30, 2016.
Extended European Search Report issued in corresponding European Patent Application No. 22178021.6, Oct. 13, 2022.
Office Action issued in parallel Chinese Patent Application No. 201980029624.7, Apr. 26, 2022, 9 pages.

* cited by examiner

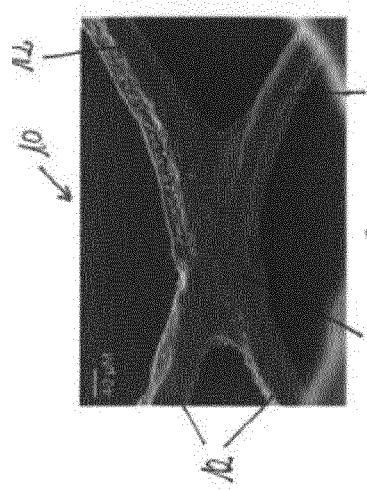
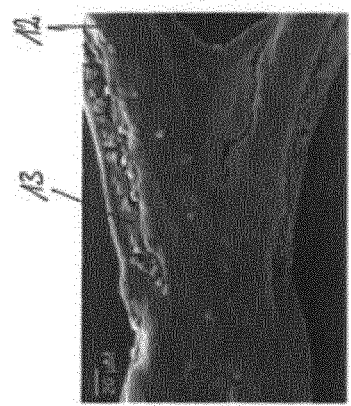
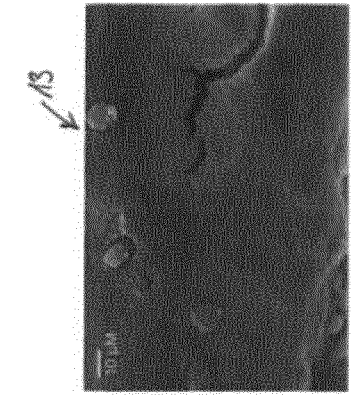
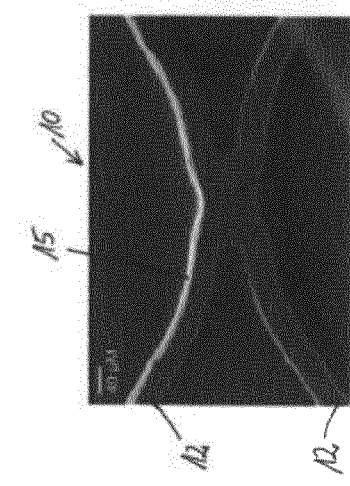
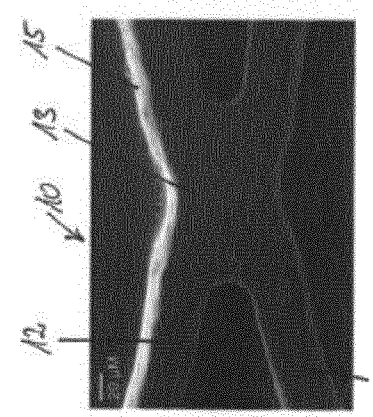
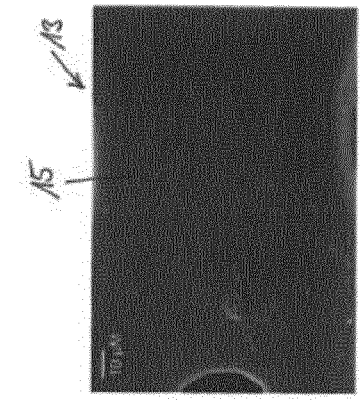

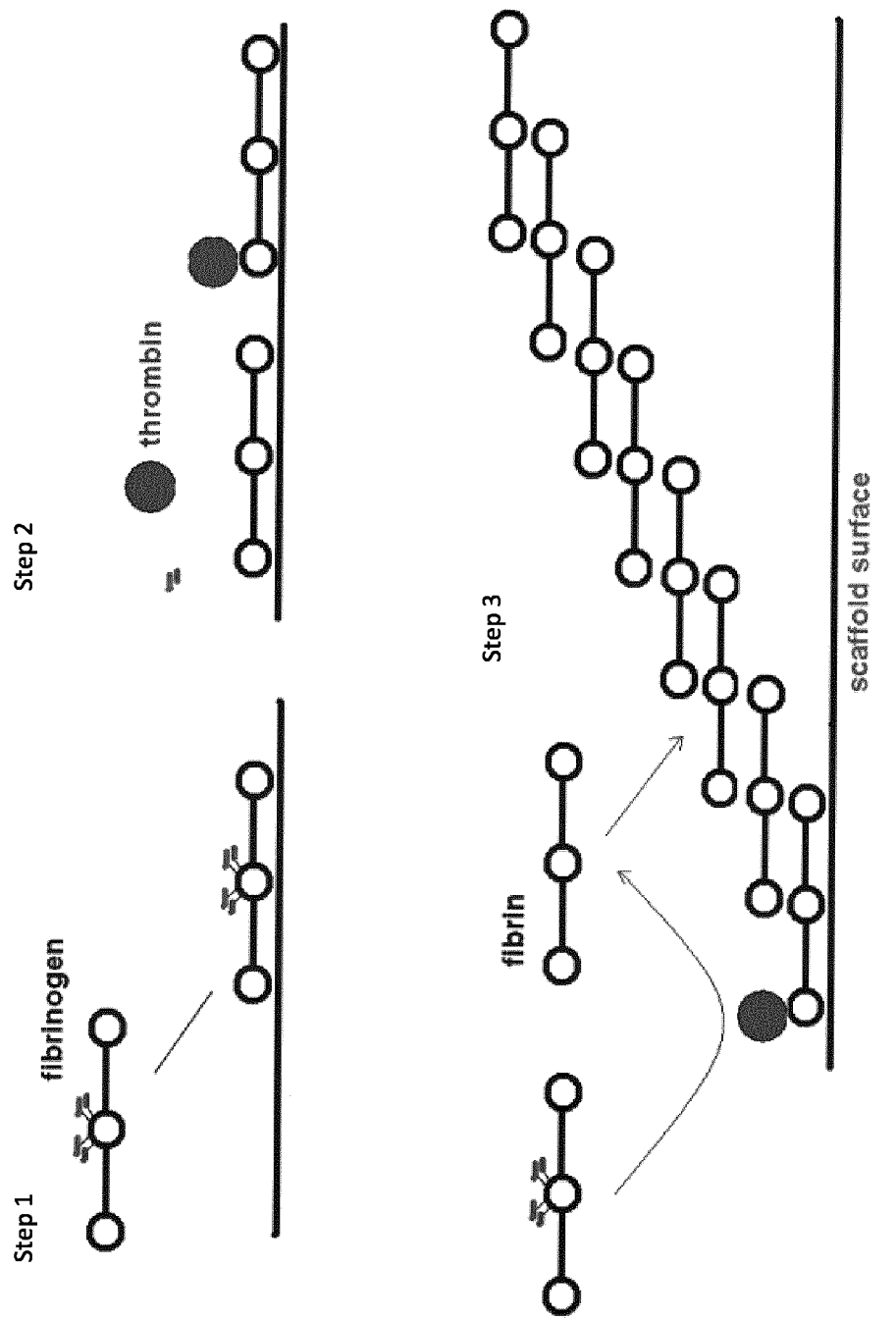

MEDICAL DEVICE AND COATING WITH BONDING AGENT

TECHNICAL FIELD

The present disclosure relates to a medical device, implant or stent and coating which includes a bonding agent for use in human vessels, a system using said medical device and a set using said medical device. A method for manufacturing said medical device is also disclosed.

BACKGROUND

In recent years medical devices used for the treatment of vascular diseases, such as aneurysms, stenoses and other neurovascular disorders, have progressed to use a self-expanding structure. These self-expanding medical devices may be flow diverters or stents, which are inserted in human vessels in order to expand said vessels, restoring the proper flow of biological fluid, restrict the flow of blood within an aneurysm or cause a clot to form within the aneurysm (in the case of stent assisted coils, they protect intra-aneurysmal coils from collapsing into the vessel lumen). The same medical devices are used to promote the endothelisation of the walls of the human vessels, however devices made of foreign material have the disadvantage of causing thrombus formation. This can lead to a vessel occlusion and, in case of neurovascular implants, to a stroke. It is thus important, that these devices don't disturb vessel reconstruction (neointima formation) and where possible promote vessel reconstruction around the implant structure. This includes the formation of a new liner of endothelial cells (endothelialisation) so that the foreign surface disappears from the circulation and risk of thrombus formation is avoided. In the case of neointima formation, this neointima should be as thin as possible, in order to avoid constriction of the lumen and thus a hypoperfusion of distal tissue. For this, endothelialisation/neointimal formation should be promoted but at the same time "controlled" to prevent a hyperplasia.

Currently available stents and flow diverters, particularly ones constructed of foreign material, may damage vessels walls through abrasion and thus trigger thrombosis. Thrombosis can also be triggered through the presence of the foreign material as well as due to a disturbed fluid dynamic at the location of the implanted device. This thrombosis within the human vessels is undesired and may lead to further narrowing as well as possible blockages of the vessels causing secondary diseases such as strokes. To avoid such occurrences patients may be administered drugs with anticoagulant properties. A disadvantage to using such medication to prevent thrombosis however, is that, since thrombus are prevented from forming, there will be increase in bleeding and thus impaired endothelialisation and wound healing. Furthermore, such a method of preventing thrombosis relies on the patient consistently taking said medication; incorrectly administering such medication may lead to a delay in endothelial regeneration. There may also be side effects for the patient when such drugs are used or alternatively patients may not respond to said drugs currently available.

In light of the above there is a need for a medical device made of a robust self-expanding non-biological material with a biological coating that is durable, promotes, or at least does not prevent, endothelisation and inhibits thrombus formation until natural endothelium is formed around the device. Furthermore, it is desirable that said medical device be compact and solve the problems discussed above.

SUMMARY

The present disclosure is designed to solve the problems previously described and relates to a medical device at least partially coated in an antithrombogenic and endothelialisation promoting coating, preferably fibrin, and formed or constructed at least partially from nickel titanium alloy. The medical device may be used as an endoluminal implant, stent or flow diverter in human vessels, in particular the carotid artery, for the treatment of neurovascular disorders or other appropriate location within the human body. As such the medical device of the present disclosure is designed such that it can be easily introduced into human vessels and also serves to avoid or reduce concomitant intake of anticoagulants.

The medical device is comprised of a self-expandable mesh structure, which at least partially forms as curved wall. This self-expanding mesh structure has both an expanded and a compressed state, the compressed state being the state prior to deployment in the human vessels and the expanded state being the state post deployment in the human vessels. The self-expandable mesh structure may, in a radially compressed state, have a cross sectional diameter of not more than 2.5 mm. In some cases, the cross-sectional diameter of the self-expandable mesh in the compressed state is preferably smaller than 0.72 mm, more preferably 0.51 mm and most preferably 0.42 mm to correspond to the insertion of catheters of 3 Fr, 2.5 Fr and 2 Fr respectively. The self-expandable mesh structure (mesh structure for short) may be formed of at least one mesh structural element or web; in this way the mesh structure may be formed of a single piece or multiple mesh structural elements. Each mesh structural elements/webs may have a height of no more than 70 μm, preferably 60 μm, preferably 50 μm, preferably 40 μm, where the height is measurable along a diameter of the mesh structure.

In this regard, it is to be noted that the inventive fibrin coating has a very stable net structure on a molecular level. Therefore, it is very durable and resists wear that is caused by guiding the medical device through small catheters, e.g. catheters smaller than 3 Fr, better than conventional coatings.

Preferably, the coating is stable or durable for such a long time that the mass of the coating is reduced by a maximum of 5%, in particular by a maximum of 3%, in particular by a maximum of 1%, over a period of at least four hours, in particular at least 30 days, when in contact with blood or a physiological substitute liquid, in particular with a sodium chloride solution or a Ringer lactate solution. This ensures that the effect of the coating lasts for a sufficiently long period of time.

The coating may be durable in such a way that the mass of the coating is completely retained over a period of at least four hours, in particular at least 30 days, when in contact with blood or a physiological replacement fluid, e.g. a sodium chloride solution or a Ringer lactate solution. Such a period makes it possible, for example, for the medical device to be coated with an endothelial cell layer so that thrombus formation is naturally prevented. The antithrombogenic coating thus bridges the period from insertion until the medical device is naturally covered or encapsulated in a neointima layer, especially of endothelial cells that form around the reticulated structural elements.

The use of a physiological replacement fluid to test the long-term resistance of the coating allows an objective comparison. Furthermore, the use of the replacement fluid, which is preferably similar to human blood, makes it possible to determine objective empirical values that indicate the behaviour of the coating in the implanted state when the coating is exposed to human blood flow. Therefore, a 0.9 percent sodium chloride solution or a Ringer lactate solution are preferably used as the replacement fluids. Such replacement fluids are isotonic and are well suited as an indicator for the behaviour of the coating in the implanted condition.

In order to prevent the coating from being rubbed off when the medical device is fed through a catheter, the coating is preferably abrasion-resistant. In particular, the coating can be so abrasion-resistant that the mass of the coating is only reduced by a maximum of 30%, in particular by a maximum of 20%, in particular by a maximum of 10%, in particular by a maximum of 5%, when the mesh structure, on which the net structure is formed, is pushed through a catheter with a length of 155 cm to 165 cm once. The coating can also be so abrasion-resistant that the mass of the coating may be completely retained when the mesh structure is pushed through a catheter with a length of 155 cm to 165 cm once. In other words, there is substantially little to no loss of the coating when guiding the medical device through a catheter towards a treatment site in a human body. Thus, the invention also provides a solution to the problem that in prior art medical devices, the coating may peel at least partially away during the delivery procedure.

The mesh structure of the medical device may be formed of a single or multiple laser cut pieces or, alternatively, a wire braid or formed by a combination of particle vapor deposition and etching construction. Preferably the implant is a permanent implant. The use of laser-cutting to form the mesh structure allows for the height, measurable along the diameter of the mesh structure, to be greatly reduced in comparison to that of a mesh structure formed of a wire braid. When the mesh structure is formed of a wire braid the cost of manufacture can be greatly reduced and, furthermore, the medical device will have a greater degree of flexibility than medical devices formed of a single piece. If a wire braid, comprising one or more wires, is used to form the mesh structure, each one of the wires may have a thickness of no more than 50 μm, particularly for stents, and no more than 45 or 40 μm for flow diverters. The structure of such devices may have a strut enlargement structures or flaps at at least some struts in order to enlarge the contact surface between the medical device and the vessel wall.

The mesh structure of the present disclosure may also have a cross-sectional diameter of in the expanded state of not more than 12 mm, in particular not more than 10 mm, in particular not more than 8 mm, and in particular not more than 6 mm, when used in the carotid artery. The mesh structure of the present disclosure may also have a cross-sectional diameter of in the expanded state of not more than 6 mm, in particular not more than 5 mm, in particular not more than 4 mm, and not less than 2.5 mm when used in intracranial vessels. The ratio of the compressed state of the mesh structure to the expanded state may be between 1:5 and 1:15, in particular between 1:8 and 1:12, preferably around 1:10. Furthermore, the curved wall of the medical device may be tubular or funnel shaped.

The fibrin coating that is applied to the mesh structure of the medical device may have a thickness of between 5 nm and 100 nm but may also have a more specific thickness of between 5 nm and 40 nm, preferably between 5 nm and 30 nm preferably between 5 nm and 20 nm, preferably between 5 nm and 15 nm, preferably 5 nm and 10 nm and most preferably 10 nm. The fibrin coating may be comprised of fibrin nanostructure (fibrin threads); these fibrin threads form a random network on the surface of the mesh structure providing additional surface area with which to bond an anticoagulant. The fibrin coating, formed on the mesh structure, may include an anticoagulant that may be heparin or other possible functional molecules, such as fibronectin. Furthermore, the fibrin coating, preferably including heparin, may be formed on all surfaces of the mesh structure, in particular all the surfaces of the mesh structural elements, such that the mesh structure is completely covered.

In addition to the excellent anticoagulant effect the coating described also supports adhesion and proliferation of vessel endothelial cells in vitro. This means that a layer of cells, especially endothelial cells, may be formed over the surface of the mesh structural elements/mesh structure.

When the anticoagulant used is heparin, heparin is covalently bonded to the fibrin coating, more specifically the fibrin nanostructure/threads. The heparin, which is covalently bonded to the fibrin coating, may be embedded in the fibrin coating. The term embedded should be understood to mean that the heparin, which is covalently bonded to the fibrin coating, forms an integral part of the coating and is ingrained in the coating. The heparin that is covalently bonded to the fibrin coating may therefore be present/found at the surface, as well as internally within, the coating. In each of these scenarios the heparin will be covalently bonded to the fibrin coating, most preferably to the fibrin threads.

When the wire braid is used to form the mesh structure the wire braid may be formed of a single wire or of multiple wires. In the case of multiple wires it is preferably for at least 12 wires to be used to form the wire braid, preferably at least 16 wires are used, most preferably for at least 24 wires to be used and even more preferably that 48 wires are used.

It is also beneficial for the mesh structural elements, and hence the mesh structure which forms the medical device, to be formed of a core of radiopaque material surrounded by an envelope of shape memory material. Suitable radiopaque materials include, for example, platinum or platinum alloys. The shape memory materials used are preferably nickel-titanium alloys, for example nitinol. The shape memory materials, in particular the nitinol material, may be treated by a surface treatment like electropolishing. That is, the medical device can have an electropolished surface. In most cases, the electropolished surface appears as slightly blue gleaming.

In some cases, the mesh structure of the medical device is covered with a covering film, which may be a fabric, nickel titanium alloy or polymeric material. This covering provides a restriction to the flow of biological fluid through the mesh structure, such that for example the flow within an aneurysm may be reduced, or is used to provide further support in the case of a stenosis.

A system is also provided which utilises the medical device along with a transport wire and a feeder tube (where the feeder tube is an appropriate introducer). The medical device is disposed on the transport wire, in particular detachably fixed to the transport wire, in a compressed state such that the medical device can be displaced in an axial direction within a feeder tube (introducer) for introduction into the human vessels. The transport wire may extend lengthwise through the mesh structure and the medical device is preferably located at a predetermined tip of the transport wire. The compressed mesh structure is also arranged with the transport wire so that it can be shifted lengthwise within the feeder tube (introducer) which preferably has a length between 25 cm and 60 cm. The medical device is therefore preferably preassembled on a transport wire and provided within the feeder tube/introducer. The feeder tube (introducer) may have an inner diameter of not more than 1.6 mm, however, the inner diameter is preferably less than this; preferably not more than 1.4 mm, preferably not more than 1.2 mm, preferably not more than 1.0 mm and most preferably not more than 0.8 mm. The feeder tube may have an inner diameter of no more than 0.7 mm, in particular no more than 0.5 mm, preferably no more than 0.4 mm and preferably corresponds to the inner diameter of a corresponding catheter used to guide the medical device to the site of treatment. This allows the medical device to be transferred to the catheter.

In this respect, it is advantageous if the system according to the invention is provided with the medical device, the transport wire and the feeder tube as a set with a catheter, whereby the catheter and the feeder tube have the same inner diameter. As far as the supply hose is concerned, it is generally intended to be made of PTFE (Polytetrafluoroethylene) or FEP (Fluorinated ethylene propylene).

A set is also provided which comprises a catheter and a previously described medical device or a previously described system, wherein the catheter has a catheter tube whose inner diameter is not more than 0.7 mm, in particular not more than 0.5 mm, and in particular not more than 0.4 mm. This corresponds, according to the unit of measure customary in medicine, to an internal diameter of about 0.027 inches, preferably a maximum of 0.027 inches, in particular a maximum of 0.021 inches, and in particular a maximum of 0.017 inches. In other words, the set preferably includes a catheter with a size of 3 French, in particular 2.5 French, especially 2 French. This concerns the outer diameter of the catheter. The above mentioned values can form maximum values and it should be understood that smaller catheter sizes are possible.

The length of the catheter tube may be between 130 cm and 170 cm, in particular between 155 cm and 165 cm, in particular 160 cm. Such a catheter length allows the catheter to be introduced into human vessels, in particular the neurovascular vascular system via peripheral blood vessels. This ensures that the catheter tip reaches the treatment site safely. The transport wire can be shifted lengthwise within the catheter tube and carry the medical device. In particular, the medical device may be attached to the distal tip of the transport wire, whereby the transport wire with the medical device can be guided through the catheter tube to the treatment site. In this case, the mesh structure of the medical device is preferably compressed, whereby a remaining inner lumen of the mesh structure is filled by the transport wire. In other words, the outer diameter of the mesh structure compressed on the transport wire is preferably equal to the diameter of the transport wire plus the double wall thickness of the mesh structure or twice the height of the mesh structure element, if the mesh structure is made up of clearly connected mesh structural elements/webs. In the case of a mesh structure consisting of a wire braid with wires that cross each other, the outer diameter of the mesh structure compressed on the transport wire is preferably the diameter of the transport wire plus the quadruple wire thickness. After discharge from the catheter tube, the medical device or the network structure can expand automatically, especially radially, and thus assume the expanded state.

Furthermore, a method is also disclosed for manufacturing the medical device described above by providing a wherein a mesh structure is provided as described above.

This mesh structure is then coated in a fibrin coating and heparin is then bonded covalently to this fibrin coating. The covalent bonding of the heparin to the fibrin coating continues until the heparin is embedded in the fibrin coating. The term embedded should be understood to mean that the heparin, which is covalently bonded to the fibrin coating, forms an integral part of the coating and is ingrained in the coating. The heparin that is covalently bonded to the fibrin coating may therefore be present/found at the surface, as well as internally within, the coating.

BRIEF DESCRIPTION OF DRAWINGS

FIGS. 2a to 2c Detailed views of a medical device with a net structure according to FIG. 1 without an inventive coating after an in vitro experiment, whereby plasma proteins are deposited;

FIGS. 3a to 3c Detailed views of an innovative medical device carrying a coating.

FIG. 4 Illustration of depicting the formation of the fibrin nanostructure on a mesh structure.

DETAILED DESCRIPTION OF THE FIGURES

Figure 1:
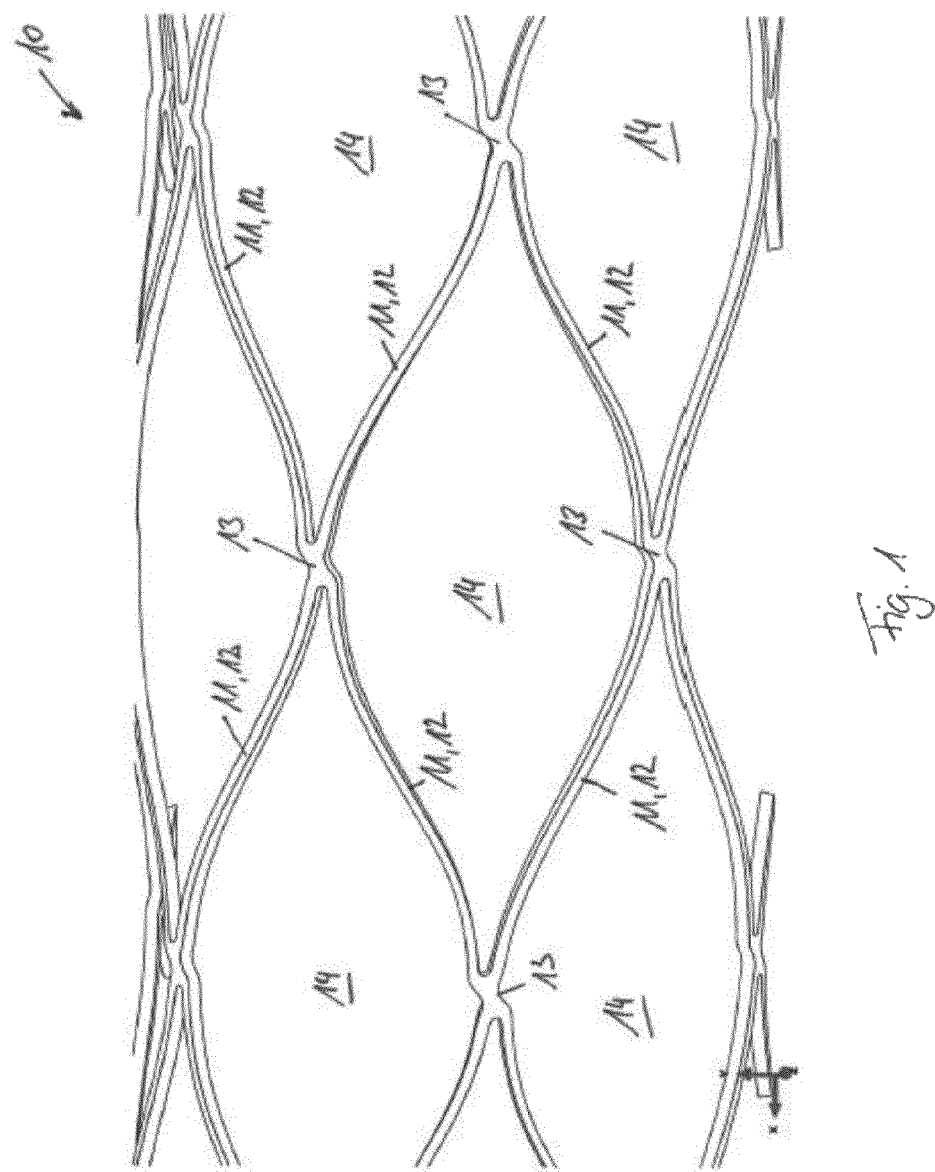
FIG. 1 A side view of a medical device which may be designed as a stent.

FIG. 1 shows in a side-view a medical device with a mesh structure 10 consisting of mesh structural elements 11. The structural elements 11 are designed as webs 12 in the design examples shown here, which may be connected together in one piece to form the mesh structure 10. It should be understood that the term mesh structural element 11/webs 12 are used to describe one part of the "wall" of each of the cells 14. The mesh structural elements 11 do not have to be connected as a single piece at each of the connectors 13. The mesh structure 10 can therefore be made from a single piece of raw material, for example by laser cutting a tube of said material, whereby the webs 12 are formed by cutting sections out of the tube material. The single piece of raw material may also be a single wire which may also form the mesh structural elements 11/webs 12s seen in FIG. 1. Alternatively, the mesh structure 10 can be produced by a physical vapour phase deposition process, e. g. a sputtering process.

FIG. 1 shows the mesh structure 10 in a partially expanded state. In particular, the mesh structure 10 according to FIG. 1, a cross-section diameter in the partially-expanded state shown, which essentially corresponds to two thirds of the cross-sectional diameter of mesh structure 10 in the fully-expanded state.

In addition to the design examples shown here, it is also possible to form the mesh structure 10 from a wire braid. The wire braid can be made up of a single wire which is deflected and returned at the longitudinal ends of the mesh structure 10. The wire may be interwoven with itself to form the mesh structure 10. The mesh structure 10 can also be made up of multiple wires that are interwoven with each other. The multiple wires may be deflected and returned at one longitudinal axial end, while the opposite longitudinal axial end may have wire ends that are open. It is also possible that the wires woven together may include open wire ends at both longitudinal axial ends.

In particular, in the case of a medical device which forms a flow diverter, at least 12, in particular 16, in particular at least 24, in particular 48 wires can form the mesh structure 10, the wires being deflected at least one longitudinal end of the mesh structure 10. This results in a mesh that has twice the number of wires, in particular 24 (fictitious), 32 (fictitious), 48 (fictitious) or 96 (fictitious) wires in one cross-section. With a view to minimizing the pore size of the mesh structure, it is intended that the braiding angle, i.e. the angle between a longitudinal axis projected in the mesh structure's wall plane and a wire of the mesh structure, is at least 65°, in particular at least 75°. In the case of a stent formed by a single wire mesh structure, the braiding angle is preferably at least 55°, in particular at least 60°, in particular at least 65°.

In the case of mesh structure 10 according to the design forms shown, webs 12 or mesh structure elements 11 may be connected to each other by connectors 13. Alternatively when a wire braid is used, the connectors 13 may be points within the mesh structure 10 where the wires cross and are interwoven with each other. Four webs 12 meet in each case in a connector 13, as shown in FIG. 1. The connector 13 may have a curved shape, which increases the flexibility of mesh structure 10 and makes it easier to introduce mesh structure 10 into small blood vessels, especially in the neurovascular area.

The mesh structure 10 forms cells 14, which are each bounded by four webs 12 in total, the basic geometry of the cells 14 is essentially, in the preferred design, diamond-shaped. FIG. 1 also indicates that the mesh structure 10 has webs 12/mesh structural elements 11 with different widths. In particular, each cell 14 is limited by two pairs of webs 12, whereby the webs 12, which are essentially parallel to each other or opposite and not directly connected to each other, form a pair of webs 12. The webs 12 of a first web pair have a smaller web width than the webs 12 of a second web pair. This arrangement of webs 12 with different web widths increase the flexibility of the mesh structure 10, thus facilitating the feeding of the medical device into human vessels, especially if these have strong vessel curvatures. The increased flexibility improves the apposition against the vascular wall and thus prevents the formation of congestive areas, which promote thrombosis. The good flexibility and the good resulting deliverability in and/or through the catheter is especially important in combination with a biological coating, preferably fibrin, more preferably fibrin including heparin.

In fact, due to the high flexibility the friction forces between the medical device and an inner surface of a catheter are relatively low. This contributes to the stability of the coating during delivery, which is also increased by the high adhesion forces provided by the very thin fibrin molecular net structure. Thus, the force needed to deliver the medical device through a catheter to a treatment site is preferably less than 1 N, in particular less than 0.8 N, preferably less than 0.7 N, preferably less than 0.6 N, more preferably less than 0.4 N. Moreover, flexibility enhances adhesion at the vessel wall in the implanted state of the medical device, preventing blood stagnation and thus reducing thrombogenicity together with the biocompatible effect of the coating itself.

In general, it is also possible for webs 12 of the mesh structure 10 to have equal web widths. Furthermore, the mesh structure 10 can have connectors 13 which are designed in such a way that there is no offset between the webs 12/mesh structural elements 11 of different cells 14. As in FIG. 1, an angle is formed between the webs 12 adjacent in circumferential direction, which are coupled to a connector 13. In the expanded state of the mesh structure 10, this cell angle is preferably between 70° and 110°, in particular 90°. In a mesh structure 10 consisting of a wire braid, the wires cross each other preferably at an angle between 100° and 140°, in particular 120°. This applies to the expanded state of mesh structure 10.

The web height can be measured along a diameter of the mesh structure 10 and is preferably no more than 70 μm, preferably 60 μm, preferably 50 μm, preferably 40 μm. The cross-sectional diameter of the mesh structure 10 in radially compressed condition shall not exceed 0.72 mm, more preferably 5.2 mm and most preferably 0.42 mm to correspond to the insertion of catheters of 3 Fr, 2.5 Fr and 2 Fr respectively. This ensures that the mesh structure 10 of the medical device can be introduced into small blood vessels, especially in the intra-cerebral area. The mesh structure (10) may have a cross-sectional diameter of in the expanded state of not more than 12 mm, in particular not more than 10 mm, in particular not more than 8 mm, and in particular not more than 6 mm, when used in the carotid artery. The mesh structure of the present disclosure may also have a cross-sectional diameter of in the expanded state of not more than 6 mm, in particular not more than 5 mm, in particular not more than 4 mm, and not less than 2.5 mm when used in intracranial vessels.

The webs 12 of mesh structure 10 also have a web width which is determined in the circumferential direction of mesh structure 10. The width of the web should preferably not exceed 50 μm, in particular 40 μm. In extreme cases or in the case of a mesh structure 10, which has webs 12 with different web widths, the narrower webs 12 may have a web width of not more than 35 μm, in particular not more than 32 μm, in particular not more than 30 μm, preferably not more than 25 μm. The minimum web width is preferably 15 μm.

Mesh structure 10 is preferably self-expandable. When the mesh structure 10 is released in a human vessel, it automatically expands into the expanded state. The mesh structure 10 of FIG. 1, may essentially be tubular or funnel shaped, or form a tubular wall. The tubular or funnel shaped wall comprises a wall thickness corresponding to the height of the webs 12. In general, mesh structure 10 can be used for different types of medical devices. It is preferable for the medical device to form a flow diverter or stent. The stent may be used for treatment of intracranial aneurysms or stenosis. Treatment of carotid artery is also possible with the medical devices disclosed herein.

In both of these cases, the mesh structure 10 is preferably designed to be rotationally symmetrical or form a substantially cylindrical wall. Alternatively, it may be provided that the medical device is designed as a flow-diverter, whereby the mesh structure 10 has a tubular or rotationally symmetrical wall in sections only. The medical device is also implantable.

The mesh structure 10 may form a stent, whereby the mesh structure 10 is produced by laser cutting or a sputtering process. Such stents preferably have a pore size which, in the expanded state of the mesh structure 10, is a maximum of 2.5 mm, in particular to a maximum of 2.0 mm, in particular to a maximum of 1.7 mm, and in particular to a maximum of 1.3 mm, in particular to a maximum of 1.1 mm. The pore size is determined by the largest possible circle that can be described in cell 14. In other words, the pore size corresponds to a maximum diameter of a cylindrical pin that can be passed through cell 14 in the expanded state of mesh structure 10. For braided stents, the pore size should preferably not exceed 1.2 mm, in particular 0.9 mm.

A stent having a laser-cut or sputtered mesh structure 10 preferably comprises between 3 and 12, in particular between 4 and 9, preferably 6, cells along the circumference of the mesh structure 10, and in the case of a braided stent, the number of cells in the circumferential direction of the mesh structure 10 preferably between 6 and 8, in particular 6.

For all types of mesh structures 10 (laser-cut, sputtered or braided) which are designed as stents, the ratio between the cross-sectional diameter of the mesh structure 10 in the compressed state and the cross-sectional diameter of the mesh structure 10 in the expanded state are preferably 1 to 5, in particular not more than 1 to 8, preferably not more than 1 to 10. For laser-cut or sputtered stents, this ratio may be less than 0.1, for example, it may not exceed 0.08. A mesh structure 10 consisting of a wire braid may in particular consist of wires, or at least one wire, which is designed as a composite wire. A composite wire of this type may have a core of radiopaque material and a layer of shape memory material completely enveloping the core. This increases the radiopaque visibility of the mesh structure 10 while maintaining the self-expandable properties. Suitable radiopaque materials include, for example, platinum or platinum alloys. The shape memory materials used are preferably nickel-titanium alloys.

If mesh structure 10 forms a medical device in the form of a flow-diverter, it is the pore size may be 500 μm at most, preferably 250 μm at most, and in particular 200 μm at most, particularly 150 μm. For very fine meshed flow diverters, for example flow diverters comprising or consisting of a graft with a polymeric layer, the pore size may be less than 0.4 mm, in particular less than 0.3 mm, preferably less than 0.2 mm, more preferably less than 0.1 mm. Moreover, due to the very thin coating it is also possible that even fine mesh structures, which are almost non-permeable and may have pores smaller then 0.1 mm, for example smaller than 50 μm, are also coated without crucially affecting the porosity.

The number of cells in circumferential direction of the mesh structure 10 is preferably between 16 and 48 for flow-diverters, in particular between 20 and 24. The webs 12 or wires of the mesh structure 10 or in general the mesh structural elements 11 of the flow-diverter cross or meet preferably at an angle between 120° and 160°, in particular 150°. In the case of flow-diverters, there is an advantageous ratio between the diameter in the compressed state of the mesh structure 10 and the diameter in the expanded state of the mesh structure 10 of at most 0.12, in particular at most 0.1, in particular at most 0.08. When the mesh structure 10 of a flow-diverter is formed from a wire braid which may have open wire ends at one longitudinal end and closed cells at the opposite longitudinal end. The closed cells may be formed by redirection of the wires at the longitudinal end of the mesh structure 10.

In the FIGS. 2a to 2c, a section of the mesh structure 10 is shown which has no coating. In particular, a connector 13 of mesh structure 10 is shown. The mesh structure 10 shown was implanted in an in vitro experiment for a period of 60 minutes into a tube with an inner diameter of 3.2 mm. The height of the mesh structure element 11 or web 12 may be no more than 70 μm. The web 12 width is 35 μm. As part of the in vitro trial, heparinized human blood at a temperature of 37° C. and a volume flow rate of 150 ml/min was passed through the tube in which the stent or mesh structure 10 was inserted. In the FIGS. 2a to 2c, a layer of blood components, which includes cells and plasma proteins, have been deposited on the mesh structure 10. Overall, it can be seen that after a short period of time untreated mesh structures 10 are "coated" with a deposit of blood components, which increases the risk of thrombosis.

In the FIGS. 3a to 3c, a section of the mesh structure 10, in particular a connector 13, is shown, whereby different magnifications are shown. In this inventive design example, the mesh structure 10 is provided at least partially with a coating 15, in particular a biofunctional coating 15. The surface or surfaces of the mesh structure 10 onto which the coating is desired to be applied to may be electropolished.

In general, it is planned that the coating 15 is not only biocompatible, but also biofunctional. This means that the coating 15 preferably promotes endothelialization, i.e. the attachment of endothelial cells. Biofunctional coating 15 can contain capture molecules such as fibronectin.

In the context of the present application, "biofunctional" does not necessarily mean that biochemical reactions are triggered by the coating. Rather, that the biofunctional coating also includes "passivation", i.e. the coating allows biological and biochemically advantageous processes, for example healing processes, to occur without interfering with them. Moreover, the biofunctional coating of the surface effects disadvantageous processes, like recruiting of inflammatory cells, proliferation of muscle cells and fibroblasts and thus hyperproliferation of the neointima tissue such that these can be avoided or reduced compared to the same surface without coating. Thus, endothelialisation or other biochemical processes depicted herein can be "provided" by the coating not by means of "activation", but through the "prevention" of other negative effects, such as thrombosis or inflammation, which may negatively affect said processes. Thus, where "promote" is described in present application, it also means "does not prevent".

The biofunctional coating 15 may be a fibrin coating. This coating 15 may be formed from a single component, fibrin, or several components, for example heparin covalently bonded to the fibrin coating 15. The thickness of coating 15 is preferably between 5 nm and 100 nm but may also have a more specific thickness of between 5 nm and 40 nm, preferably between 5 nm and 30 nm preferably between 5 nm and 20 nm, preferably between 5 nm and 15 nm, preferably 5 nm and 10 nm and most preferably 10 nm. The coating 15 may have a thickness that can be determined, for example, using a scanning force microscope (atomic force microscopy/AFM measuring method).

The fibrin coating 15 may be formed on the mesh structure 10, in particular the mesh structural elements 11/webs 12, as indicated in FIG. 4. The fibrin coating 15 may completely cover the mesh structure 10; in particular the mesh structural elements 11/webs 12. Alternatively, or additionally, the activation of the material surface, e.g. with plasma or functional groups, or chemical activation may be applied.

Alternatively, the fibrin coating 15 may be formed on an intermediate layer between the mesh structure 10 and the fibrin coating 15. This intermediate layer may be an adhesive layer to promote the adhesion of fibrin to the mesh structure 10. When an intermediate layer is used between the mesh structure 10 and the fibrin coating the fibrin may be formed on said intermediate layer in the same manner as described below.

FIG. 4 depicts the formation of the fibrin coating 15 from fibrinogen at a substrate surface. As can be seen in FIG. 4 fibrinogen may be applied to the surface of the mesh structure through absorption (Step 1). When the surface is then exposed to thrombin solution, thrombin may be attached to the absorbed fibrinogen via biospecific noncovalent binding (Step 2). When the surface is subsequently exposed to a fibrinogen solution, the immobilized thrombin converts fibrinogen, approaching the surface from the solution, to fibrin monomers that associate spontaneously to a network of fibrin threads at the substrate surface (Step 3). The growth of the fibrin network can be stopped by replacing the fibrinogen solution with a buffer. The coatings thickness can be decreased when anticoagulant Antithrombin III (AT III) is added to the fibrinogen solution. A very thin fibrin network can be obtained by adding a mixture of AT III and heparin. AT III and heparin are then removed from the final coating by washing with a buffer.

In this way the thickness of the coating 15 can be controlled to be as desired by the user but preferably between 5 nm and 100 nm. The fibrin coatings described above can be formed on virtually any substrate including surfaces of a medical device. The coatings are biodegradable and biocompatible.

The fibrin coating may be functionalised by covalent attachment of chemically activated anticoagulant heparin. This functionalisation decreases thrombogenicity of the coating. The chemical activation of heparin may be performed, e.g. by reaction with sodium periodate. The fibrin coating may be prepared from fibrinogen solution containing AT III and heparin, and may be functionalised by the covalent attachment of chemically activated heparin. The functionalised fibrin coating may contain between 0.5 and 3 $\mu g/cm^2$, preferably between 1.0 and 2.0 $\mu m/cm^2$, preferably between 1.2 and 1.6 $\mu m/cm^2$, preferably between 1.3 and 1.5 $\mu m/cm^2$ of fibrin and between 5 and 50 $mU/cm^2$, preferably between 7 and 30 $mU/cm^2$, more preferably between 10 to 20 $mU/cm^2$, in particular 12 to 18 $mU/cm^2$, and most preferably approximately 15 $mU/cm^2$ of heparin, wherein 180 U of heparin corresponds to 1 mg of heparin; these values may vary +/−20%. The functionalised coating considerably improves the hemocompatibility of the substrate (mesh) surface.

The amount of fibrin can be measured by using a bicinchoninic acid (BCA) kit assay. The BCA method allows for measuring a concentration of a protein like fibrin, in a solution. The amount of heparin can be measured by using a colormetric assay.

It has been discovered that the above amounts of fibrin and heparin improve the stability of the coating significantly and allow for a smooth guidance of the stent through a catheter.

The heparin may continue to be covalently bonded to the fibrin coating 15 such that the heparin is embedded in the fibrin coating 15. The bonded heparin forms an integral part of the coating 15 and is ingrained in the coating 15. The heparin that is covalently bonded to the fibrin coating 15 may therefore be present/found at the surface, as well as internally within, the coating 15.

The heparin may be covalently bonded to the fibrin coating 15 as discussed above. This bonding of an active biomolecule to the fibrin coating 15, formed of fibrin nanostructures, improves hemocompatibility and promotes attachment and proliferation of vascular endothelial cells.

In addition or alternatively to the fibrin coating 15 of the mesh structure 10, the mesh structure 10 may be wholly or partially covered in a covering film. This covering film may be formed of a number of appropriate thin materials, however, it is preferable that the covering film be made of fabric, nickel titanium alloy or a polymeric material. Alternatively, the covering film may be formed of the fibrin threads which form the fibrin nanostructure network as the coating 15 as discussed above. This covering film may be a very thin sheet (film) of material that covers at least part of either the outer surface of the mesh structure 10 or the internal surface of the mesh structure 10. Alternatively, there may be covering films which cover both the inner and outer surfaces of the mesh structure 10 with a small gap between them corresponding to the height of the mesh structural elements 11/webs 12. The advantage of providing the mesh structure 10 of the medical device with at least one covering film is that a larger surface area can be provided onto which a fibrin coating 15 can be applied. A further advantage is that the covering film, which may have micro pores, can more readily control the flow of biological fluids through the cells 14 of the mesh structure 10 during the treatment of the stenosis of human vessels or more particularly aneurysms.

The antithrombogenic coating, heparin, bridges the period of time until natural healing or encapsulation of the medical device in a neointimal layer, especially from endothelial cells that form around the mesh structural elements.

REFERENCE NUMERALS

10 Mesh structure
11 Mesh structural element
12 Web
13 Connectors
14 Cell
15 Coating

The invention claimed is:

1. A medical device for use in human vessels comprising:
   a self-expandable mesh structure which at least partially forms a curved wall, and has, in a radially compressed state, a cross-sectional diameter of not more than 2.5 mm,
   wherein the mesh structure is formed of at least one mesh structural element which has a height that is no more than 200 μm, where the height is measurable along a diameter of the mesh structure, and
   wherein the mesh structure is at least partially formed of a nickel titanium alloy and is at least partially coated in fibrin,
   wherein the fibrin coating has a thickness between 5 nm and 100 nm.

2. The medical device of claim 1, wherein the mesh structure is formed from at least one lasercut piece.

3. The medical device of claim 1, wherein the mesh structure is formed using one or more wires.

4. The medical device of claim 3, wherein each of the one or more wires has a thickness of no more than 50 μm.

5. The medical device of claim 3, wherein the wire is comprised of at least 12 wires forming a wire braid.

6. The medical device of claim 1, wherein the fibrin coating includes heparin covalently bonded to the fibrin.

7. The medical device of claim 6, wherein the heparin is embedded in the fibrin coating.

8. The medical device of claim 1, wherein the mesh structure has a cross sectional diameter in the expanded state of not more than 12 mm.

9. The medical device of claim 1, wherein the curved wall is tubular or funnel shaped.

10. The medical device of claim 1, wherein the fibrin coating, including heparin, is formed on at least the inner and/or outer peripheral surface of the mesh structure or wherein the mesh structure is completely covered in fibrin.

11. The medical device of claim 1, wherein the ratio of the cross-sectional diameter of the mesh structure from the compressed state to the expanded state is between 1:5 and 1:15.

12. The medical device of claim 1, wherein the mesh structural elements are formed of a core of radiopaque material and an envelope of shape memory material.

13. The medical device of claim 1, wherein the mesh structure is covered with a covering film.

14. The medical device of claim 13, wherein the covering film is fabric, nickel titanium alloy or polymeric material.

15. The medical device of claim 1, wherein the fibrin coating contains between 0.5 and 3 µg/cm² of fibrin.

16. The medical device of claim 1, wherein the fibrin coating contains between 5 and 50 mU/cm² of heparin.

17. A set comprising:
a catheter, and
a medical device according to claim 1,
wherein the catheter comprises a catheter tube having an inner diameter of not more than 1.6 mm.

18. A medical device comprising:
a self-expandable mesh structure which at least partially forms a curved wall, and has, in a radially compressed state, a cross-sectional diameter of not more than 1 mm,
wherein the mesh structure is formed of at least one mesh structural element which has a height that is no more than 70 µm, where the height is measurable along a diameter of the mesh structure, and
wherein the mesh structure is at least partially formed of a nickel titanium alloy and is at least partially coated in fibrin,
wherein the fibrin coating has a thickness between 5 nm and 100 nm.

19. The medical device of claim 18, wherein the medical device is used for neurovascular disorders.

20. A system comprising:
a medical device according to claim 1, and
a transport wire,
wherein the medical device is disposed on the transport wire in a compressed state such that the medical device is axially displaceable within a feeder tube, and
wherein the feeder tube has an inner diameter of not more than 1.6 mm.

21. A method of manufacturing a medical device, in which the following steps are performed:
providing a self-expandable mesh structure for a medical device according to claim 1;
forming a fibrin coating on the mesh structure, covalently bonding heparin to the fibrin coating.

22. The method of claim 21, wherein the covalent bonding of heparin to the fibrin coating is continued until the heparin is embedded in the fibrin coating.

* * * * *